(12) United States Patent
Matsukawa (10) Patent No.: US 9,733,461 B2
(45) Date of Patent: Aug. 15, 2017

(54) PHOTO-STIMULATOR AND MICROSCOPE SYSTEM

(71) Applicant: OLYMPUS CORPORATION, Shibuya-ku, Tokyo (JP)

(72) Inventor: Yasunari Matsukawa, Saitama (JP)

(73) Assignee: OLYMPUS CORPORATION, Tokyo (JP)

(*) Notice: Subject to any disclaimer, the term of this patent is extended or adjusted under 35 U.S.C. 154(b) by 165 days.

(21) Appl. No.: 14/580,133

(22) Filed: Dec. 22, 2014

(65) Prior Publication Data

US 2015/0177502 A1 Jun. 25, 2015

(30) Foreign Application Priority Data

Dec. 24, 2013 (JP) .................... 2013-265243

(51) Int. Cl.
| | |
|---|---|
| *H04N 9/47* | (2006.01) |
| *H04N 7/18* | (2006.01) |
| *G02B 21/00* | (2006.01) |
| *G02B 21/16* | (2006.01) |
| *G01N 21/64* | (2006.01) |

(52) U.S. Cl.
CPC ..... *G02B 21/0032* (2013.01); *G02B 21/0076* (2013.01); *G02B 21/16* (2013.01); *G01N 21/6458* (2013.01); *G01N 2021/6471* (2013.01); *G01N 2201/0675* (2013.01)

(58) Field of Classification Search
CPC  G02B 21/0032; G02B 21/16; G02B 21/0076; G01N 21/6458; G01N 2021/6471; G01N 2201/0675

USPC ....................................................... 348/78, 79
See application file for complete search history.

(56) References Cited

U.S. PATENT DOCUMENTS

| | | | |
|---|---|---|---|
| 2005/0263690 A1* | 12/2005 | Araya ................. | G02B 26/101 250/234 |
| 2008/0055493 A1 | 3/2008 | Hanano | |
| 2009/0015530 A1 | 1/2009 | Goetz et al. | |
| 2011/0002019 A1* | 1/2011 | Routley ................. | G02B 27/48 359/9 |
| 2011/0109958 A1 | 5/2011 | Yokoi | |

(Continued)

FOREIGN PATENT DOCUMENTS

| | | |
|---|---|---|
| EP | 1895363 A2 | 3/2008 |
| JP | 2008083661 A | 4/2008 |

(Continued)

*Primary Examiner* — Jared Walker
(74) *Attorney, Agent, or Firm* — Holtz, Holtz & Volek PC (57) ABSTRACT

To avoid unstable light radiation during switching of a phase modulation amount and stimulate desired stimulation points simultaneously, provided is a photo-stimulator which includes an AOM switching on/off of radiation of stimulation light to a specimen S; an LCOS-SLM being capable of modulating a phase of stimulation light once radiation to the specimen S has been turned on by the AOM; and a controller controlling the LCOS-SLM to switch a phase modulation amount of stimulation light and controlling the AOM to switch on/off of radiation of stimulation light, wherein the controller causes the AOM to turn off radiation of stimulation light before the LCOS-SLM starts switching a phase modulation amount, and causes the AOM to turn on radiation of stimulation light after the LCOS-SLM completes switching a phase modulation amount.

5 Claims, 5 Drawing Sheets

(56) References Cited

U.S. PATENT DOCUMENTS

2011/0267663 A1* 11/2011 Murayama ............... G03H 1/08
                                                        359/9
2013/0222443 A1    8/2013 Goetz et al.
2013/0342768 A1* 12/2013 Yokoyama ............ G02F 1/1313
                                                        349/1

FOREIGN PATENT DOCUMENTS

| JP | 2009540341 A  | 11/2009 |
| JP | 2011099986 A  | 5/2011  |
| JP | 2011133580 A  | 7/2011  |
| WO | 2007143105 A2 | 12/2007 |

* cited by examiner

PHOTO-STIMULATOR AND MICROSCOPE SYSTEM

CROSS REFERENCE TO RELATED APPLICATIONS

This application is based on Japanese Application No. 2013-265243, the contents of which are incorporated herein by reference.

TECHNICAL FIELD

The present invention relates to a photo-stimulator and a microscope system.

BACKGROUND ART

Conventionally, a pupil modulation technique using an LCOS-SLM (liquid crystal on silicon-spatial light modulator) is known (see PTL 1, for example). A phase modulation type spatial optical modulation element including an LCOS element can arbitrarily change phase distribution of light that is incident on a pupil of an objective lens, thereby forming multiple spots simultaneously on a position of an image so that it is possible to stimulate simultaneously a plurality of stimulation points on a specimen.

CITATION LIST

Patent Literature

{PTL 1} Japanese Unexamined Patent Application, Publication No. 2011-133580

SUMMARY OF INVENTION

Solution to Problem

A first aspect of the present invention is a photo-stimulator including a switching part switching on/off of radiation of stimulation light to a specimen; a phase modulating part being capable of modulating a phase of stimulation light once radiation to the specimen has been turned on by the switching part; and a controlling part controlling the phase modulating part to switch a phase modulation amount of stimulation light and controlling the switching part to switch on/off of radiation of stimulation light, wherein the controlling part causes the switching part to turn off radiation of stimulation light before the phase modulating part starts switching a phase modulation amount, and causes the switching part to turn on radiation of stimulation light after the phase modulating part completes switching a phase modulation amount.

DESCRIPTION OF EMBODIMENTS

First Embodiment

Hereinafter, descriptions will be given of a photo-stimulator and a microscope system according to a first embodiment of the present invention with reference to the drawings.

Figure 1:
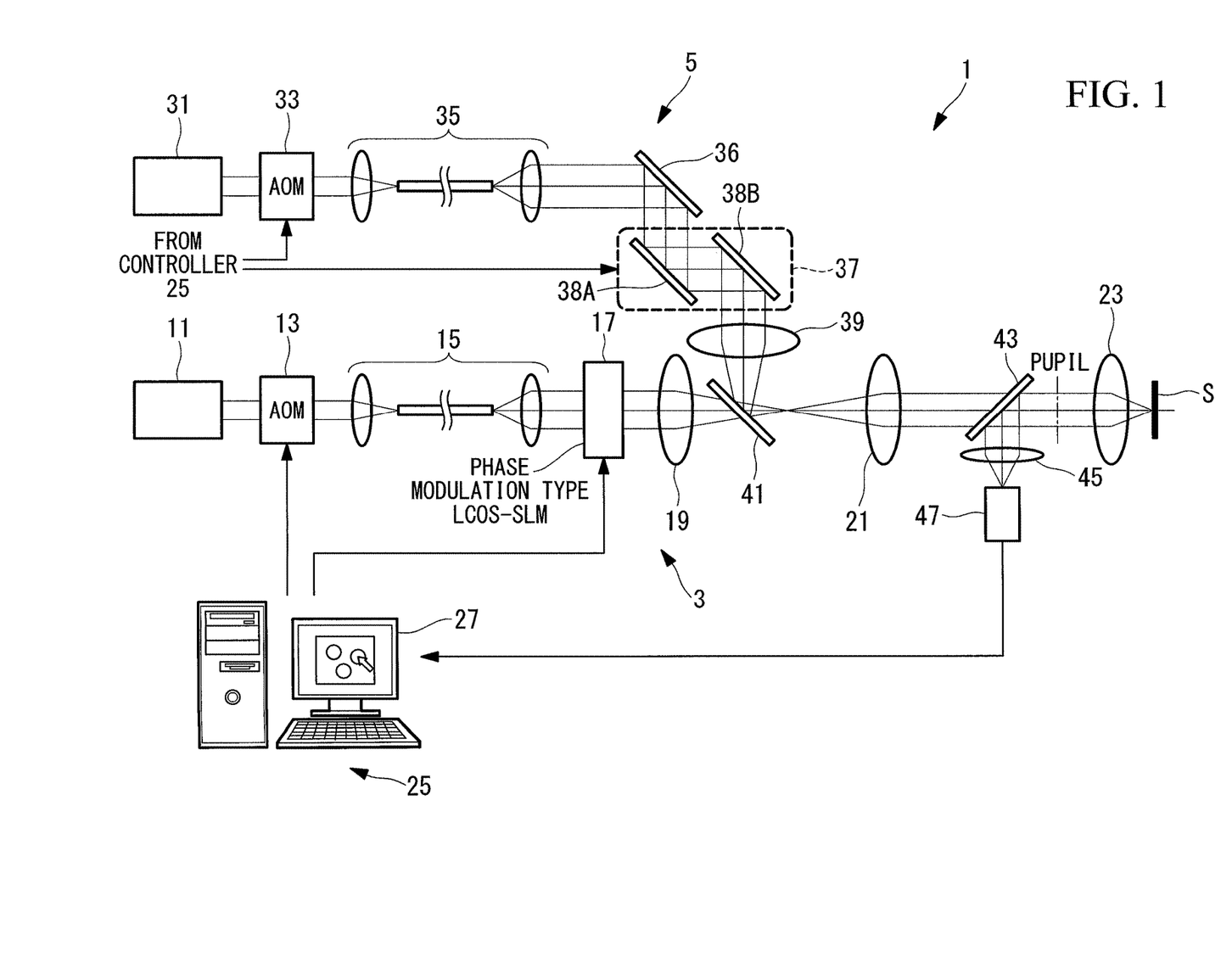
FIG. 1 is a schematic diagram illustrating a microscope system according to a first embodiment of the present invention.

A multiphoton excitation (MPE) laser microscope system (hereinafter, referred to as microscope system) 1 according to the present embodiment includes a photo-stimulator 3 stimulating a specimen S with light, and an imaging apparatus 5 generating an image of the specimen S, as shown in FIG. 1.

The photo-stimulator 3 includes an ultrashort pulse laser (light source, hereinafter referred to as stimulating laser) 11 emitting a stimulation laser beam (hereinafter referred to as stimulation light), an AOM (acousto-optic modulator, acousto-optical element, switching part) 13 turning on/off radiation and performing intensity modulation of stimulation light emitted from the stimulating laser 11, an introducing optical system 15 converting stimulation light having passed through the AOM 13 to parallel light, an LCOS-SLM (liquid crystal on silicon-spatial light modulator, phase modulating part) 17 being capable of modulating a phase of stimulation light which has been converted to parallel light, and a pupil projecting lens 19 condensing stimulation light having passed through the LCOS-SLM 17.

The photo-stimulator 3 also includes an image forming lens 21 converting stimulation light condensed by the pupil projecting lens 19 to parallel light, an objective lens 23 radiating the specimen S with stimulation light having been converted to parallel light by the image forming lens 21 and collecting return light from the specimen S, and a controller (controlling part) 25 performing control of the AOM 13 and the LCOS-SLM 17, etc. The photo-stimulator 3 can stimulate the specimen S with light at any timing regardless of operating or non-operating of the imaging apparatus 5.

The imaging apparatus 5 includes an ultrashort pulse laser (light source, hereinafter referred to as exciting laser) 31 emitting an excitation laser beam (hereinafter, referred to as excitation light), an AOM 33 turning on/off radiation and performing intensity modulation of excitation light emitted from the exciting laser 31, an introducing optical system 35 converting stimulation light having passed through the AOM 33 to parallel light, a reflecting mirror 36 reflecting excitation light having been converted to parallel light, a scanner (scanning part) 37 deflecting excitation light reflected by the reflecting mirror 36, a pupil projecting lens 39 condensing excitation light deflected by the scanner 37, and a combining DM (dichroic mirror) 41 combining excitation light condensed by the pupil projecting lens 39 to an optical path of stimulation light of the photo-stimulator 3.

Moreover, the imaging apparatus 5 shares the image forming lens 21, the objective lens 23 and the controller 25 of the photo-stimulator 3, in which the image forming lens 21 converts excitation light combined to the optical path of stimulation light by the combining DM 41 to parallel light, and the objective lens 23 radiates the parallel light to the specimen S. Also, the imaging apparatus 5 controls the AOM 33 and the scanner 37 with the controller 25, and generates an image of the specimen S.

Furthermore, the imaging apparatus 5 includes an excitation DM 43 separating, from the optical path of the photo-stimulator 3, a fluorescence which is generated on the specimen S through radiation of excitation light and collected by the objective lens 23, a condensing lens 45 condensing a fluorescence separated by the excitation DM 43, and a PMT (photomultiplier tube) 47 detecting and photoelectrically converting a fluorescence condensed by the condensing lens 45 to send a light intensity signal, which corresponds to luminance, to the controller 25.

Under the control by the controller 25, the AOMs 13 and 33 can switch on/off of radiation of stimulation light emitted from the stimulating laser 11 and excitation light emitted from the exciting laser 31 to the specimen S, and control such stimulation light and excitation light.

The LCOS-SLM 17, which has, for example, 1920×1080 pixels (illustration omitted), is arranged at a position conjugate to a pupil position of the objective lens 23. Moreover, under the control by the controller 25, the LCOS-SLM 17 can change a phase of stimulation light to any degree within the range from 0 to $2\pi$ [rad] at each pixel to transmit the resultant light. As a result, the LCOS-SLM 17 causes three-dimensional change of intensity distribution of stimulation light on the specimen S so that the specimen S can be radiated in a desired three-dimensional pattern as a Fourier-transformed image.

The scanner 37, which is a so-called proximity galvanoscanner, includes two galvanomirrors 38A and 38B which are arranged so as to face each other. Under the control by the controller 25, the scanner 37 oscillates two galvanomirrors 38A and 38B respectively around axes (XY) orthogonal to each other so that excitation light is deflected by raster scanning operation. As a result, the scanner 37 can scan on the specimen S two-dimensionally with exciting light.

The combining DM 41 transmits stimulation light condensed by the pupil projecting lens 19 of the photo-stimulator 3. Also, the combining DM 41 reflects excitation light condensed by the pupil projecting lens 39 of the imaging apparatus 5 so that the optical path of the stimulation light and the optical path of the excitation light are combined.

The excitation DM 43 transmits stimulation light or excitation light from the image forming lens 21 to cause the light to enter the objective lens 23. Also, the excitation DM 43 reflects, toward the condensing lens 45, a fluorescence collected from the specimen S by the objective lens 23 to separate the optical path of the fluorescence from the optical path of the excitation light.

The controller 25 controls the on/off switching of radiation of stimulation light and excitation light by the AOMs 13 and 33, the phase modulation amount switching of stimulation light by the LCOS-SLM 17, the switching of a swing angle of the galvanomirrors 38A and 38B by the scanner 37, and capture of a light intensity signal from the PMT 47 in such a manner that all are temporally synchronized.

In the case where the LCOS-SLM 17 switches a radiation pattern of stimulation light, the controller 25 causes the AOM 13 to turn off radiation of stimulation light to the specimen S before a phase modulation amount of the stimulation light starts to be switched. Furthermore, the controller 25 causes the AOM 13 to turn on radiation of stimulation light to the specimen S after the LCOS-SLM 17 completes switching the phase modulation amount of the stimulation light.

Moreover, the controller 25 integrates light intensity signals sent from the PMT 47 for each pixel corresponding to a scanning point of the scanner 37 so that a two-dimensional image of the specimen S is generated. The controller 25 includes a monitor 27, and thus, the generated image can be displayed on the monitor 27.

Descriptions will be given of the operation of the photo-stimulator 3 and the microscope system 1 having the aforementioned configuration.

In order to obtain an image of the specimen S with the imaging apparatus 5 of the microscope system 1 of the present embodiment, the exciting laser 31 emits excitation light, and the AOM 33 turns on radiation of excitation light to the specimen S and adjusts an amount of the excitation light. Excitation light adjusted by the AOM 33 is deflected by the scanner 37 through the introducing optical system 35 and the reflecting mirror 36, is condensed by the pupil projecting lens 39, and is combined to the optical path of the photo-stimulator 3 by the combining DM 41.

Excitation light combined to the optical path of the photo-stimulator 3 is converted to parallel light by the image forming lens 21 to penetrate the excitation DM 43, and is radiated to the specimen S by the objective lens 23. As a result, the specimen S is two-dimensionally scanned with excitation light based on the swing angles of the galvanomirrors 38A and 38B of the scanner 37.

When radiation of excitation light generates a fluorescence on the specimen S, the fluorescence is collected by the objective lens 23, is separated from the optical path of excitation light by the excitation DM 43, and is detected by the PMT 47 through the condensing lens 45. In the PMT 47, a detected fluorescence is photo-electrically converted so that a light intensity signal, which corresponds to luminance, is sent to the controller 25.

The controller 25 integrates light intensity signals sent from the PMT 47 for each pixel corresponding to a scanning point of the scanner 37, and generates a two-dimensional image of the specimen S so that the controller 25 causes the monitor 27 to display the generated image. As a result, a user can observe the specimen S on the monitor 27.

Next, in order to stimulate the specimen S with light by the photo-stimulator 3, the stimulating laser 11 emits stimulation light, and the AOM 13 turns on radiation of stimulation light to the specimen S and adjusts an amount of the stimulation light. Stimulation light adjusted by the AOM 13 enters the LCOS-SLM 17 through the introducing optical system 15, the phase of the stimulation light is modulated so as to obtain, for example, a desired pattern of three-dimensional intensity distribution on the specimen S (for example, referred to as pattern 1), and the resultant light penetrates the LCOS-SLM 17.

Stimulation light having penetrated the LCOS-SLM 17 is condensed by the pupil projecting lens 19 to penetrate the combining DM 41, and is converted to parallel light by the image forming lens 21. Stimulation light having been converted to parallel light penetrates the excitation DM 43 and is radiated to the specimen S by the objective lens 23. Consequently, it is possible to simultaneously stimulate a plurality of radiation points on the specimen S with light in the intensity distribution of the pattern 1, which corresponds to the phase modulation amount by the LCOS-SLM 17.

As a result, for example, while the imaging apparatus 5 obtains the image of the specimen S, the photo-stimulator 3 stimulates the specimen S with light, and thus, it is possible to observe a reaction of the specimen S stimulated with light on the monitor 27.

Furthermore, the controller 25 causes the LCOS-SLM 17 to switch a phase modulation amount of stimulation light, whereby allowing simultaneous photo-stimulation of a plurality of radiation points on the specimen S in another pattern having different intensity distribution (for example, referred to as pattern 2).

Here, the LCOS-SLM 17 has a liquid crystal panel structure, and thus, it takes at least a few to several dozens of milliseconds or more to switch a phase modulation amount. If stimulation light is radiated in the duration when the LCOS-SLM 17 switches a phase modulation amount, it is impossible to anticipate which point an image of stimulation light to penetrate each pixel is formed at. Accordingly, if stimulation light is radiated on the LCOS-SLM 17 at an early timing before completion of the switching of a phase modulation amount, the stimulation light may be radiated on an unintended point.

Figure 2:
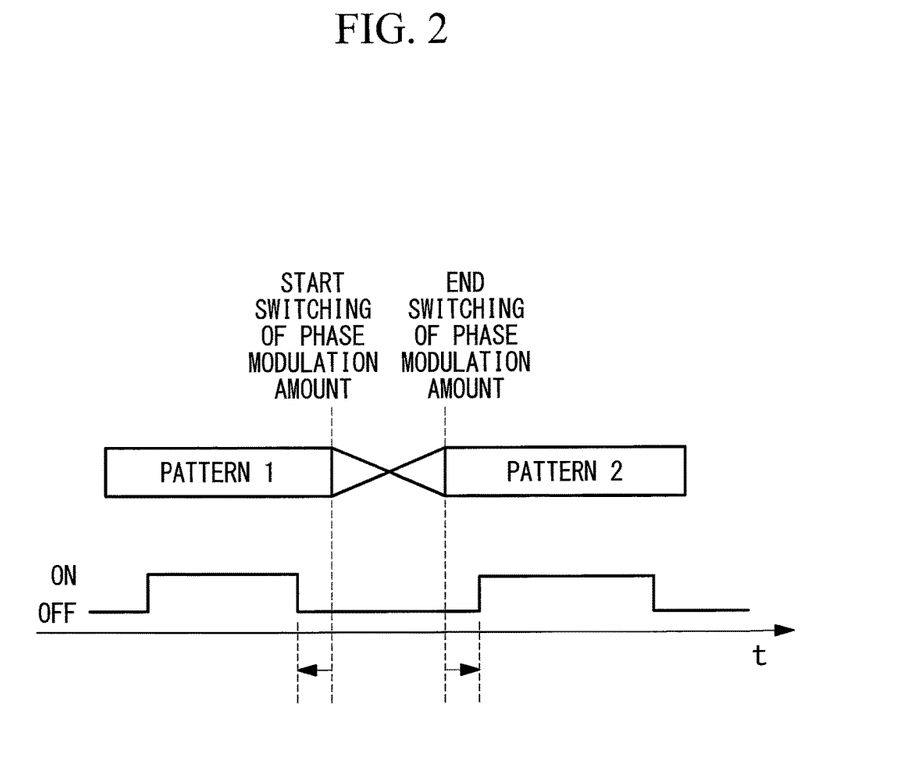
FIG. 2 illustrates an example of relationship between a timing at which an LCOS-SLM switches a phase modulation amount of stimulation light and a timing at which an AOM turns on/off radiation of stimulation light to a specimen, in the microscope system of FIG. 1.

In contrast, in the photo-stimulator 3, shortly before the controller 25 causes the LCOS-SLM 17 to start switching the pattern 1 to the pattern 2, that is, shortly before the switching of a phase modulation amount of stimulation light starts (approximately one millisecond before, in the typical case where an AOM is used for intensity modulation), the AOM 13 turns off radiation of stimulation light, as shown in FIG. 2. Furthermore, shortly after the LCOS-SLM 17 completes switching to the pattern 2, that is, shortly after the switching of a phase modulation amount is completed (approximately one millisecond after, in the typical case where an AOM is used for intensity modulation), the AOM 13 turns on radiation of stimulation light.

As a result, it is limited to before the LCOS-SLM 17 starts switching a phase modulation amount and after the LCOS-SLM 17 completes switching the phase modulation amount when radiation of stimulation light to the specimen S is performed. During switching of a phase modulation amount, radiation of stimulation light to the specimen S is stopped. The abscissa in FIG. 2 indicates time (t).

As described so far, according to the photo-stimulator 3 and the microscope system 1 of the present embodiment, the controller 25 causes the AOM 13 to turn on/off radiation of stimulation light so as to prevent radiation of stimulation light in the duration when the LCOS-SLM 17 switches a phase modulation amount, and it is thereby possible to prevent the LCOS-SLM 17 which is switching a phase modulation amount from radiating light on an unintended point. Therefore, unstable light radiation during switching of a phase modulation amount can be avoided, and thus, desired stimulation points can be stimulated simultaneously. Moreover, by the imaging apparatus 5, it is possible to observe a reaction of the specimen S stimulated with light on the monitor 27.

In the example shown in FIG. 2, radiation of stimulation light to the specimen S is turned off shortly before the LCOS-SLM 17 starts switching a phase modulation amount of stimulation light, and radiation of stimulation light to the specimen S is turned on shortly after the LCOS-SLM 17 completes switching the phase modulation amount of stimulation light. However, it is sufficient that stimulating light is prevented from being radiated to the specimen S in the duration when the LCOS-SLM 17 switches a phase modulation amount. For example, radiation of stimulation light to the specimen S may be turned off almost the same time as the LCOS-SLM 17 starts switching a phase modulation amount of stimulation light, and radiation of stimulation light to the specimen S may be turned on almost the same time as the LCOS-SLM 17 completes switching the phase modulation amount of stimulation light.

In FIG. 1 for illustrating the present embodiment, an example of the phase modulating part is a transmission type LCOS-SLM (LCOS-SLM 17) changing a phase of transmitted light. However, even when a reflection type LCOS-SLM changing a phase of reflected light is used, the essence of the present invention is the same. The same is applied to variations described below.

A possible variation of the present embodiment is as follows.

Figure 3:
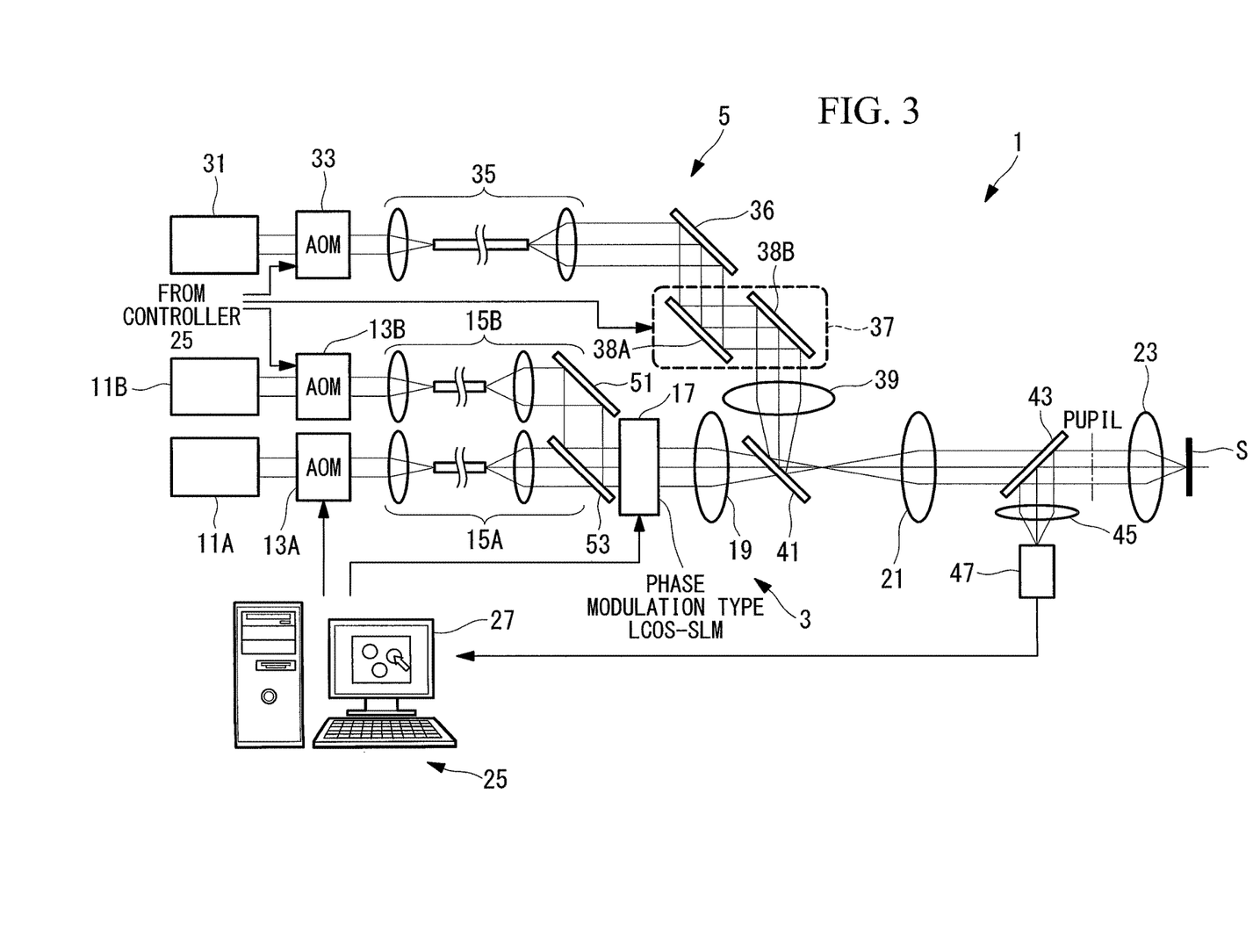
FIG. 3 is a schematic diagram illustrating a microscope system according to a first variation of the first embodiment of the present invention.

Specifically, in the present embodiment, the photo-stimulator 3 includes the single stimulating laser 11 and the single AOM 13. In contrast, in a first variation, the photo-stimulator 3 may include two or more stimulating light sources 11A and 11B having different wavelengths and AOMs 13A and 13B not depending on each other, the AOMs 13A and 13B may independently switch on/off of stimulation lights emitted from the stimulating light sources 11A and 11B, respectively, and phases of stimulation lights having passed through the AOMs 13A and 13B may be modulated by the common LCOS-SLM 17, for example, as shown in FIG. 3.

The photo-stimulator 3 may also include an introducing optical system 15B converting stimulation light, which has been emitted from the stimulating light source 11B and passed through the AOM 13B, to parallel light, a reflecting mirror 51 reflecting stimulation light having been converted to parallel light by the introducing optical system 15B, and a combining DM 53 combining stimulation light reflected by the reflecting mirror 51 to an optical path of stimulation light of a set of the stimulating light source 11A, the AOM 13A and an introducing optical system 15A, and the controller 25 may control the AOMs 13A and 13B, independently.

For example, the specimen S may be stimulated with stimulation light having one wavelength from the stimulating laser 11A, e.g., in the intensity distribution of the pattern 1, and the specimen S may be stimulated with stimulation light having another wavelength from the stimulating laser 11B, e.g., in the intensity distribution of the pattern 2.

In this case, while stimulation light from the stimulating laser 11A is adjusted by the AOM 13A and the specimen S is stimulated with light in the pattern 1, the AOM 13B may turn off radiation of stimulation light from the stimulating laser 11B. Also, while stimulation light from the stimulating laser 11B is adjusted by the AOM 13B and the specimen S is stimulated with light in the pattern 2, the AOM 13A may turn off radiation of stimulation light from the stimulating laser 11A.

Also in the present variation, in the case where the LCOS-SLM 17 switches a phase modulation amount of stimulation light, the controller 25 may cause the AOMs 13A and 13B to turn off radiation of stimulation lights from the stimulating lasers 11A and 11B, respectively, before the LCOS-SLM 17 starts switching a phase modulation amount of stimulating light, and the AOMs 13A and 13B to turn on radiation of stimulation lights from the stimulating lasers 11A and 11B, respectively, after the LCOS-SLM 17 completes switching the phase modulation amount.

The present variation is preferable for a case where different points on the specimen S is stimulated with light not only for the purpose of varying stimulation points on the specimen S, but also for the purpose of activating different functions of the specimen S such as activating or suppressing an ion channel formed by combining channelrhodopsin and halorhodopsin, for example.

Figure 4:
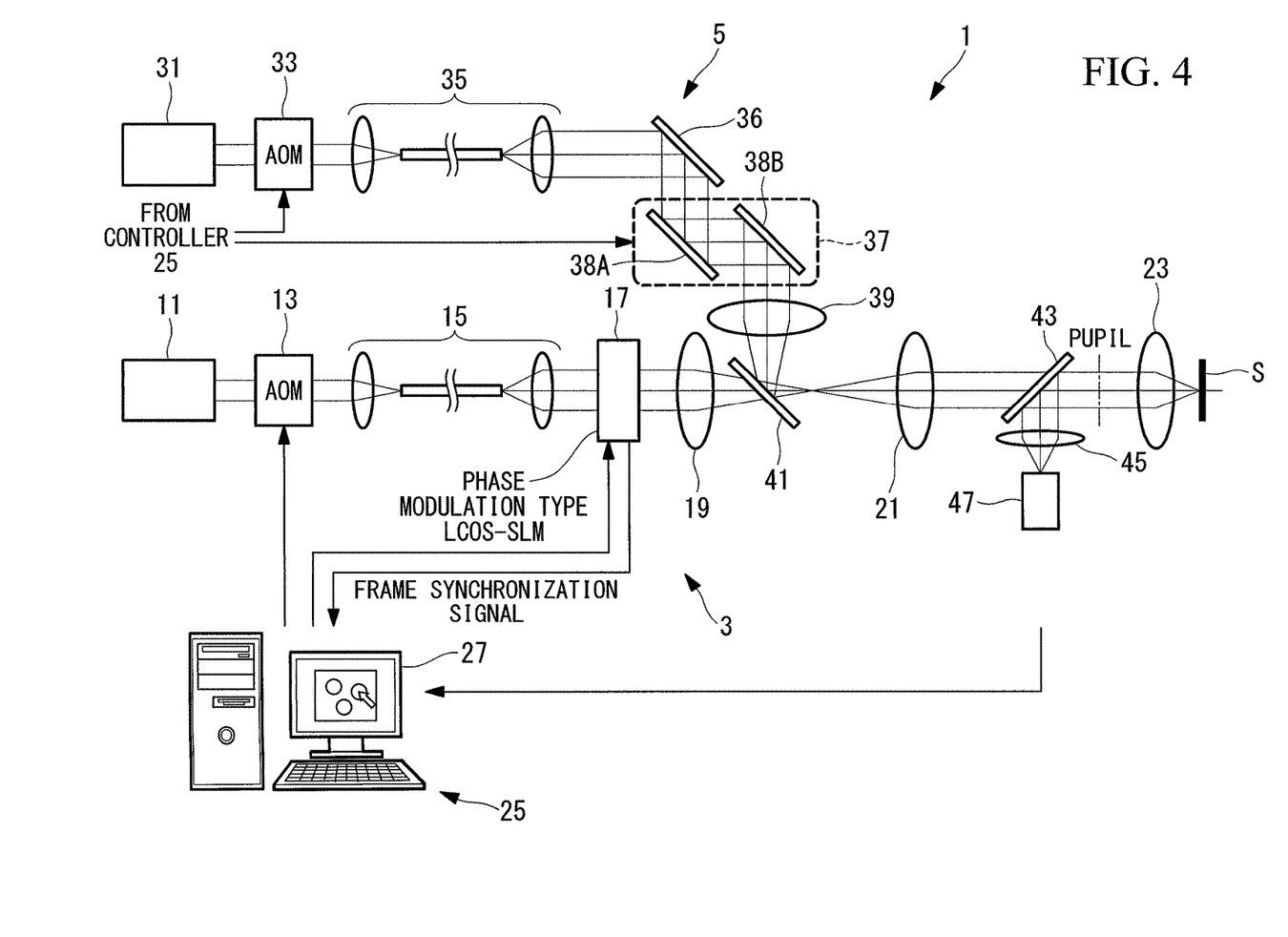
FIG. 4 is a schematic diagram illustrating a microscope system according to a second variation of the first embodiment of the present invention.

Next, in a second variation, the LCOS-SLM 17 may set special distribution of a phase modulation amount according to a predetermined frame data. Moreover, as shown in FIG. 4, the controller 25 may capture a frame synchronization signal corresponding to the frame data of the LCOS-SLM 17, the AOM 13 may switch on/off of radiation of stimulation light to synchronize with the frame synchronization signal.

Figure 5:
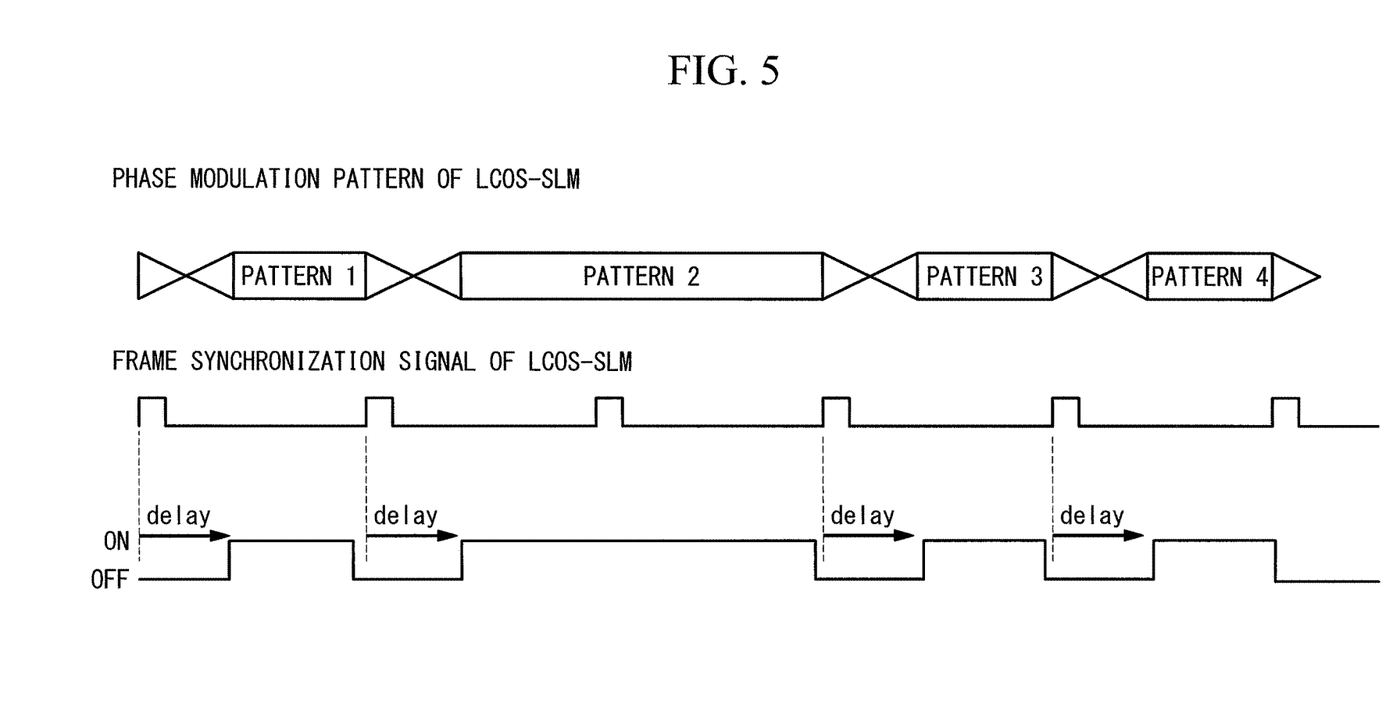
FIG. 5 illustrates an example of relationship between a timing at which an LCOS-SLM switches a phase modulation amount of stimulation light and a timing at which an AOM turns on/off of radiation of stimulation light to a specimen, in the microscope system of FIG. 4.

For example, as shown in FIG. 5, in a case where the LCOS-SLM 17 starts switching a phase modulation amount at a rising edge of the frame synchronization signal, the controller 25 may set the rising edge of the frame synchronization signal of the LCOS-SLM 17 as a time reference and cause the AOM 13 to turn off radiation of stimulation light before the timing reference. Moreover, the controller 25 may cause the AOM 13 to turn on radiation of stimulation light after a predetermined delay time period, which is from the timing reference to completion of the phase modulation amount switching, has elapsed, and thus, the phase modulation amount may be switched to a desired modulating amount.

Moreover, the duration time in which the AOM 13 keeps radiation of stimulation light on is determined by the controller 25 in advance, and thus, when radiation of stimulation light is to be continued over two or more cycles of the frame synchronization signal, the AOM 13 may perform no on/off operation even if a rising edge of the synchronization signal, which is a timing reference, is detected, as illustrated as the pattern 2 in FIG. 5.

As a result of this, the controller 25 can easily cause the AOM 13 to switch radiation of stimulation light to the specimen S while avoiding a time period of switching a phase modulation amount according to the predetermined frame data of the LCOS-SLM 17.

In the present variation, the controller 25 may set a falling edge of the frame synchronization signal of the LCOS-SLM 17 as a timing reference.

The embodiment of the present invention has been described in detail so far with reference to the drawings. A specific configuration is, however, not limited to the above embodiment, and the present invention also encompasses a design, a variation and the like within the gist of the present invention. For example, without being limited to the aforementioned embodiment and variations, the present invention may be applied to an embodiment which combines the above embodiment and the above variations as appropriate. The present invention is not particularly limited.

Furthermore, in place of the stimulating light sources 11, 11A, 11B and the exciting light source 31, a visible CW laser (continuous wave laser) may be used, for example. Moreover, the imaging apparatus 5 may include a confocal pinhole which transmits light generated at the focal position of the objective lens 23 on the specimen S only, among fluorescences condensed by the condensing lens 45.

From the above-described embodiment, the following inventions are derived.

The first aspect of the present invention is a photo-stimulator including a switching part switching on/off of radiation of stimulation light to a specimen; a phase modulating part being capable of modulating a phase of stimulation light once radiation to the specimen has been turned on by the switching part; and a controlling part controlling the phase modulating part to switch a phase modulation amount of stimulation light and controlling the switching part to switch on/off of radiation of stimulation light, wherein the controlling part causes the switching part to turn off radiation of stimulation light before the phase modulating part starts switching a phase modulation amount, and causes the switching part to turn on radiation of stimulation light after the phase modulating part completes switching a phase modulation amount.

According to the above configuration, when the switching part turns on radiation of stimulation light to the specimen, the phase modulating part modulates the phase of the stimulation light and then the resultant light is radiated on the specimen. As a result, it is possible to stimulate a plurality of radiation points on the specimen with light simultaneously, according to a phase modulation amount by the phase modulating part. Furthermore, when the switching part turns off radiation of stimulation light to the specimen, photo-stimulation of the specimen is stopped.

In this case, when, in order to prevent radiation of stimulation light in the duration when the phase modulating part switches a phase modulation amount, the controlling part causes the switching part to switch on/off of radiation of stimulation light, it is possible to prevent the phase modulating part which is switching a phase modulation amount from radiating light on an unintended point. Therefore, unstable light radiation during switching of a phase modulation amount can be avoided, and desired stimulation points can be stimulated simultaneously.

In the first aspect, the phase modulating part can set special distribution of a phase modulation amount according to a predetermined frame data, and the controlling part may cause the switching part to switch on/off of radiation of stimulation light to synchronize with a frame synchronization signal corresponding to the frame data of the phase modulating part.

According to this configuration, the controlling part can easily cause the switching part to switch radiation of stimulation light while avoiding a time period of switching a phase modulation amount according to the predetermined frame data of the phase modulating part.

A second aspect of the present invention is a microscope system including; an imaging apparatus including a scanning part scanning a specimen by excitation light emitted from a light source and an image generating part detecting return light from the specimen to generate an image of the specimen, the return light caused by the scanning part scanning the specimen by the excitation light; and any one of the photo-stimulators described above.

According to this configuration, unstable light radiation during switching of a phase modulation amount can be avoided by the photo-stimulator, and a reaction of the specimen stimulated with light can be observed as an image by means of the imaging apparatus.

REFERENCE SIGNS LIST

1 Microscope system
3 Photo-stimulator
5 Imaging apparatus
13, 13A, 13B AOM (switching part)
17 LCOS-SLM (phase modulating part)
25 Controller (controlling part, image generating part)
37 Scanner (scanning part)
S Specimen

The invention claimed is:

1. A photo-stimulator comprising:
a switching device which switches radiation of stimulation light to a specimen on and off;
a phase modulator which is configured to modulate a phase of the stimulation light; and
a controller which controls the phase modulator to switch a phase modulation amount of the stimulation light and controls the switching device to switch the radiation of the stimulation light on and off,
wherein:

the controller controls the switching device to turn off the radiation of the stimulation light before the phase modulator starts switching the phase modulation amount, and controls the switching device to turn on the radiation of the stimulation light after the phase modulator completes switching the phase modulation amount, the phase modulator is further configured to set a spatial distribution of the phase modulation amount according to predetermined frame data, and the controller controls the switching device to switch the radiation of the stimulation light on and off so as to synchronize with a frame synchronization signal corresponding to the predetermined frame data.

2. A microscope system comprising:
an imaging apparatus including:
  a scanner which scans a specimen by excitation light emitted from a light source; and
  an imaging device which detects return light from the specimen to generate an image of the specimen, the return light being caused by the scanner scanning the specimen by the excitation light; and
the photo-stimulator according to claim 1.

3. A photo-stimulator comprising:
a shutter which switches radiation of stimulation light to a specimen on and off;
a phase modulator which is configured to modulate a phase of the stimulation light; and
a controller which controls the phase modulator to switch a phase modulation amount of the stimulation light and controls the shutter to switch the radiation of the stimulation light on and off,
wherein:
the controller controls the shutter to turn off the radiation of the stimulation light before the phase modulator starts switching the phase modulation amount, and controls the shutter to turn on the radiation of the stimulation light after the phase modulator completes switching the phase modulation amount,
the phase modulator is further configured to set a spatial distribution of the phase modulation amount according to predetermined frame data, and
the controller controls the shutter to switch the radiation of the stimulation light on and off so as to synchronize with a frame synchronization signal corresponding to the predetermined frame data.

4. A microscope system comprising:
an imaging apparatus including:
  a scanner which scans a specimen by excitation light emitted from a light source;
  a detector which detects return light from the specimen, the return light being caused by the scanner scanning the specimen by the excitation light; and
  an image generator which generates an image of the specimen based on signals sent from the detector; and
the photo-stimulator according to claim 3.

5. The photo-stimulator according to claim 3, wherein the shutter comprises an acousto-optic modulator.

* * * * *